United States Patent
Holt et al.

(10) Patent No.: US 6,573,302 B1
(45) Date of Patent: *Jun. 3, 2003

(54) CREAM UTILIZING CAPSAICIN

(75) Inventors: Stephen D. Holt, Little Rock, AR (US); Teresa Leigh Barr, Port Townsend, WA (US)

(73) Assignee: Medical Merchandising, Inc., Little Rock, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/056,630

(22) Filed: Jan. 25, 2002

Related U.S. Application Data

(63) Continuation-in-part of application No. 09/662,962, filed on Sep. 15, 2000, now Pat. No. 6,348,501, which is a continuation of application No. 09/408,740, filed on Sep. 29, 1999, now Pat. No. 6,197,823.

(51) Int. Cl.$^7$ ................................................ A61K 31/16
(52) U.S. Cl. ...................................................... 514/627
(58) Field of Search .......................................... 514/627

(56) References Cited

U.S. PATENT DOCUMENTS 6,197,823 B1 * 3/2001 Barr et al. .................. 514/627
6,348,501 B1 * 2/2002 Holt et al. .................. 514/627

* cited by examiner

*Primary Examiner*—Theodore J. Criares
*Assistant Examiner*—Jennifer Kim
(74) *Attorney, Agent, or Firm*—Wendy Buskop; Buskop Law Group, P.C.

(57) ABSTRACT

A cream comprising: a topical carrier wherein the topical carrier comprises a member selected from the group comprising lavender oil, myristal myristate, and other preservatives including, hypericum perforatum arnica montana capric acid; and 0.01 to 1.0 wt. % capsaicin; 2 to 10 wt. % an encapsulation agent selected from the group comprising colloidal oatmeal hydrogenated lecithin, dipotassium glycyrlhizinate and combinations thereof; esters of amino acid; a light scattering element having a particle size up to 100 nm.; and a histidine.

16 Claims, No Drawings

CREAM UTILIZING CAPSAICIN

This application is a continuation-in-part of application of Ser. No. 09/662,962 filed Sep. 15, 2000, now U.S. Pat. No. 6,348,501 which is a continuation-in-part of Ser. No. 09/408,740 filed Sep. 29, 1999 now U.S. Pat. No. 6,197,823.

BACKGROUND OF THE INVENTION

Arthritis is a common chronic problem, which occurs below the surface of the skin. Millions of people and animal have the condition. Various topical creams and ointments are sold for treatment of arthritis; however, most utilize an anesthetic, such as lidocane, benzocaine or other numbing agent for the skin surface.

The present invention was developed to provide a cream, which has as the three critical ingredients, capsaicin, plus an anesthetic and an analgesic. The composition overcomes other obstacles of known capsaicin creams in that the amounts used enable the warming relief of the peppers in combination with the coolness of the anesthetic, yet enable the user to still feel objects they touch due to the use of an analgesic as a critical component rather than large amounts of anesthetics.

Various capsaicin compositions have been developed over the years, in particular, the psoriatic composition of U.S. Pat. No. 4,486,450, the nasal composition of U.S. Pat. No. 5,134,166, and the composition of U.S. Pat. No. 4,997,853, the anti-inflammatory composition of U.S. Pat. No. 5,560,910, the composition of U.S. Pat. No. 5,962,532, the composition for animals of U.S. Pat. No. 5,916,565, the stomach treatments of U.S. Pat. No. 5,889,041, the composition of U.S. Pat. No. 5,827,886, the patch with medication of U.S. Pat. No. 5,741,510, all of which are incorporated by reference herein.

After many years of research and testing on subject, the present invention has been developed which does not rely on topical anesthetics, such as lidocaine (Entry 5310, p. 786 Merck Index, Tenth Edition 1983) and benzocaine (ethyl aminobenzoate, Entry 3710, p. 546 Merck Index, Tenth Edition, 1983) into formulations containing capsaicin, and then applying such formulations for the initial period of treatment to eliminate the painful burning from the application of capsaicin, allowing the patient to continue therapy while being able to feel through the skin onto which the cream is applied.

SUMMARY OF THE INVENTION

The present invention relates to a method of treating arthritis using a cream composition therefore in which capsaicin is used as the principle therapeutic agent along with an analgesic and an anesthetic in a cream.

An object of the present invention is to provide a cream, which is easily applied, easy to absorb into the skin, and provides ability to feel objects.

DETAILED DESCRIPTION OF THE PREFERRED EMBODIMENT

Capsaicin is trans-8-methyl-N-vanillyl-5 nonenamide, a naturally occurring alkyl vanillylamide and a type of capsaicinoid. It is found in high concentration in fruit of plants of the Capsicum genus. The chili pepper, red pepper and paprika are all species of Capsicum. All hot papers contain capsaicinoids. Capsaicinoids are natural materials, which produce a burning sensation in the mouth. Capsicum has recently been officially defined in the USP 23 where it is defined as the dried ripe fruit of *Capsicum frutescens* Linne or *Capsicum annum* Linne.

There are two main capsaicinoids, capsaicin and dihydrocapsaicin and three minor capsaicinoids, nordihydrocapsaicin, homocapsaicin and homodihydrocapsaicin. All capsaicinoids are considered usable within the scope of this invention.

Capsicum is the dry powder obtained by grinding up the fruits of these plants. Capsicum oleoresin (or capsaicin oleoresin) is the liquid concentrate extracted from the dry powder. Capsaicin, a white crystalline material, is obtained from the liquid concentrate.

The composition of the invention comprises capsaicin as a first active ingredient and at least one second active ingredient acting as an analgesic to reduce the sensation of capsaicin induced skin irritation. The ingredients are contained in a carrier fluid. The genus capsicum is a member of a large tropical family solanaceae. There are numerous species, of which *Capsicum annum, Capsicum chinense* and *Capsicum frutescens* are closely related. *Capsicum frutescens* is also known as Cayenne Pepper, Chili Pepper, Pimento Tabasco Pepper and Tabasco-sauce pepper.

Capsaicin (N-Vanillyl-8-methyl-6-(E)-noneamide) is the most pungent of the capsaicinoids. It is very soluble in fats, oils and alcohols. Capsicum also contains a red coloring matter, oleic acid, palmitic acid and stearic acid.

*Capsicum frutescens* extract can be obtained from Bio-Botanica, Inc. of Hauppauge, N.Y. and appears as a viscous fluid, having a sallow yellow color, a caustic and pungent aroma, and is soluble in ethanol.

Capsicum is a powerful local stimulant. It is strongly rubifacient acting without vesication.

In the present invention, capsaicin is mixed with a carrier fluid. Preferably, the carrier fluid is water-based and forms an aqueous solution containing the ingredients. However, the carrier may be a fluid such as an oil based carrier, a fat based carrier, a fatty alcohol based carrier and combination of these.

Additional irritant is added to the capsaicin and carrier. Histidines, such as histamine dihydrochloride, are considered usable in the scope of the present invention to create vasodilatation, and act as a second irritant. Adding the second irritant produces an analgesic effect and does not numb the site, like an anesthetic or depress coetaneous sensory receptors. It is possible to add more than one histidine to achieve the analgesic reaction. Instead, it has a topical counterirritant effect by stimulating coetaneous sensory receptors, see, Federal Register, Vol. 48, No. 27, Tuesday Feb. 8, 1983, pages 5367 et. seq. Local anesthetics, such as benzocaine and lidocaine, act differently as anesthetics not producing an analgesic effect which is achieved by adding an additional irritant, such as a histamine hydrochloride or most preferably a histamine dihydrochloride. If a histamine dihydrochloride is used, it is preferred to use a starting composition of 98% histamine, although compositions in the range of 96–99% histamine will be usable as well.

Generally speaking, the cream will contain in the range of 0.00125% to 1% by weight of capsaicin. Compositions containing more than 1% by weight of capsaicin will provide a therapeutic effect, with up to 62% by weight capsaicin, except that the burning side effect will increase in proportion to the increase percentage of capsaicin. Compositions containing 0.025% to 20% by weight of capsaicin could be used. Compositions of 0.025 to 2% by weight are considered usable as well. Compositions containing in the range of 0.025% to 0.25% by weight of capsaicin are preferred because they are narrowly encompassed within current FDA guidelines regarding capsaicin use. However, the FDA guidelines were developed at a time when there was not an effective method for relieving the discomfort generated by capsaicin. The present invention provides a method to increase the amount of capsaicin that can be administered comfortably.

In the present invention, capsaicin is mixed with a carrier fluid to formulation. Preferably, the carrier is water-based and forms a cream containing ingredients that quickly soak into the skin, providing fast transdermal absorption. However, the carrier may be a fluid such as an oil-based carrier, a fat based carrier, a fatty alcohol based carrier or combination of these, or an omega-6 fatty acid.

The novel cream uses an encapsulation agent, colloidal oatmeal, or hydrogenated lecithin, dipotassium glycyrrhizinate or a similar encapsulation agent, or even combinations of these agents, to be effective. The colloidal oatmeal has intrinsic SFP, natural sunscreen capability. In addition, the colloidal oatmeal encapsulates the capsaicin to reduce the inflammation effect the capsaicin has on the skin, while still enabling the capsaicin to work effectively. Typically, up to 3-wt. % colloidal oatmeal is used in this invention, although any amount of about between 2 wt. % and up to about 10-wt. % can be used. The colloidal oatmeal works within the scope of this invention because it contains hydrophilic colloids. These colloids help to provide a protective barrier on the skin to control inflammation. In addition, histidines, such as L-histidines, are present in colloid oatmeal. Histidines can be present in the oats in weight percents up to 3% of the total amino acids in the oats. The invention has found that using the colloidal oats enhance, synergistically the histamine dichlorohydride effect, when histamine dichlorohydride is used.

The unique formulation is a topically (externally) applied formulation which has three simultaneous effects, analgesic, anesthetic and antipruritic effects, by (1) depressing cutaneous sensory receptors to relieve pain and (2) stimulating cutaneous sensory receptors using a topical counter irritant, with a fast, transdermal absorption.

It is the combination of analgesic and anesthetic which make this invention unique.

Any one of the following histidines, or combinations thereof, are considered usable in this invention. L-histidines, histamine dihydrocholoride, DL-histidine, D-histidine hydrochloride monohydrate, L-histidine hydrochloride monohydrate, L-histidine methyl ester dihydrochloride, L-histidinol dihydrochloride, histamine phosphate.

Titanium dioxide, with or without the aluminum is typically dispersed in caprylic/capric triglyceride, causing this component to contain approximately 50% by weight of solids.

Titanium dioxide is considered the best light scattering element for the present invention. Titanium dioxides usable within the scope of the present invention are preferably fine particle or pigmentary titanium dioxides available from Solaveil, of Durham, England. Any of the Solaviel $TiO_2$ products for cosmetic use can be used. All will reflects ultraviolet and provide broad UVB light protection, effectively scattering the light rays. In a preferred embodiment, the $TiO_2$ can provide a complete block of sunlight, and when mixed with the colloidal oatmeal, the lightwaves can be refracted and the skin protected from burning from the light.

Other than titanium dioxides, other components can be used for the light scattering purpose. For example, octyl dodecyl neopentanoate, can be used for light scattering. Bernell Chemical sells these compounds. Zinc oxide can be used as light scattering component, which also has the advantage of being anti-itch, or anti-pruritic effect.

Titanium dioxide, with or without the aluminum is typically dispersed in caprylic/capric triglyceride.

It should be noted that other additives may be used in the present invention such as xanthum gum, myristal mystereate polyethylene glycols (PEG's) and other stearates for coagulation of the compound.

"Lavender flower oil" or lavender oil, and a "bergaptene-free" bergamot oil or bergamot extract, can be beneficial in that the lavender is an active transdermal activator which causes the formula to penetrate the skin; rather than remaining on the surface of the skin. Lavender oil and bergamot extract is also beneficial in that both provides muscle relaxant characteristics and the bergamot oil also provides help with acne, fevers, herpes, and diabetic neuropathy. Between 1–4 wt % of lavender oil is needed for transdermal activation, but between 0.5 and 5.0 wt percent could be used.

The cream also can include the following:

1. *Arnica montana;*
2. *Hypericum perforatum* (known as St. John's Wort);
3. *Aloe barbadensis* gel;
4. Citric acid to adjust the pH of the compound;
5. Propylene glycol with methyl and propyl parabens as preservatives;
6. A chealating agent to keep the product from separating, such as edetatedisodium;
7. Triethanolamine hydrochloride which acts as a reagent; and
8. Other preservatives and Benzoin derivatives.

Still others considered usable in the present invention are phenoxy ethanol, ethyl paraben, and butyl paraben as preservatives, or in the preservative system. Other ingredients such as inositol, methyl paraben, propyl paraben, hydroxy ethyl cellulose can be used therein.

Xanthum gum is be added to the invention to provide a higher density compound, and act as a thickening agent. Other elements, such as licorice extract, glycerial polymethacrytate and hydroxypropyl cellulose could be used in various formulations of the basic invention.

A suspension agent can be added to the formula of the present invention. Alkyl benzoate is considered usable within the scope of the present invention, and helps to suspend the particle size of the colloidal oatmeal and titanium dioxide.

The present invention is fast acting and long acting due to the menthol present in the compositions. The uses of the invention are contemplated for post perpetic neuralgia, and scar conditions after surgery, such as for treating the scars from a mastectomy. Also, the present invention is considered usably for victims of neuropathy, such as diabetes with neuropathy.

In the method of the invention, a victim of pain or discomfort is treated by applying the above-described composition topically to the skin of the victim near an area affected by the pain or discomfort. The types of pain or discomfort to which the invention may be applied include those discussed in the background of the invention. Generally speaking, the inventive composition, a cream, is applied to the selected area, such as a joint, and rubbed in. The amount applied is not critical. Generally, it should be applied in an amount, which is sufficient to cover the area of application. Usually, the amount used will be in the range of from about 0.3 to about 3 ccs.

For the treatment of pruritus or itching, the application of the composition can be repeated as required to control the discomfort. When the preferred composition of the invention is applied, it provides near immediate relief from the itching caused by poison ivy or hemorrhoids, without a burning sensation. The relief lasts for several hours. It is surprising that a capsaicin based composition would be useful for the treatment of such discomfort. To enhance the antipruritic effect, additional compounds can be added to the formulation. These components can be methyl sulphonyl methane, sodium bicarbonate, calamine, allatoin, kaolin, and combinations thereof.

For best results in the treatment of arthritis, the treatment should be repeated several times per day, such as in the range of 2 to 8 times per day, preferably 3–5 times per day, and continued for several days. Surprisingly, most patients do not experience the burning discomfort heretofore known as a very common side effect of topical capsaicin application.

The foregoing is a description of the composition and method of use of three embodiments of the invention. The scope of the invention is considered to include the described embodiment together with others obvious to those skilled in the art.

In the present invention, capsaicin is distributed accordingly to known techniques in various pharmaceutically acceptable carriers to form a cream. Some of these carriers contain volatile diluents such as alcohol and may contain various emulsifying and suspending agents.

The present invention involves the use of an analgesic and an anesthetic in combination to produce a warm sensation on the patient's skin without the usual burning side effects of traditional capsaicin ointments or gels.

The following example demonstrates the invention.

EXAMPLE 1

Cream Formulation

A cream which is representative of the present invention includes but are not limited to the following:

| INGREDIENT | WT % |
|---|---|
| Deionized water | q.s. |
| Propylene glycol | 5.00 |
| Triethanolamine | 0.40 |
| Edetate disodium | 0.02 |
| Methyl paraben | 0.30 |
| Propyl paraben | 0.10 |
| Lavender extract | 2.0 |
| Bergamot extract | 1.0 |
| Capsaicin | 0.025–0.25% |
| Xanthum gum | 0.30 |
| Histamine dihydrochloride | 0.025–1.0% |
| Hypericum pergoratum extracts | 1.0 |
| Arnica montana extract | 1.0 |
| Aloe barbadensis gel | 1.0 |
| Alkyl benzoate | 11.0 |
| Colloidal oatmeal | 3.0 |
| Dipotassium glycyrrhizinate | 1.0 |
| Hydrogenated lecithin | 1.0 |
| Stearates and PEG's | 2.0 |
| Other preservatives, benzyl alcohol | 1.5 |
| Menthyl lauryl pidolate | 4.03 |
| Cyclomethicone | 5.0 |
| Titanium dioxide solution | 3.0 |
| Citric acid | Q.S. |
| Myristal myristate | Q.S. |

EXAMPLE 2

A Cream Which Has the Formulation

The present invention contemplates the following formulation for a cream comprising:

0.01 to 0.25 wt % Capsaicin;

1 to 10 wt % Glycerol Monosterate;

1 to 10 wt % Polysorbate;

5 to 15 wt % Titanium Dioxide;

5 to 14 wt % Benzyl Alcohol;

2 to 10 wt % Colloidal Oatmeal;

0.5 to 4 wt % Lavender Oil;

1 to 2 wt % Propylene Glycol;

0.0001 to 0.005 wt % Xanthum Gum;

0.1 to 0.005 wt % Uniphen P-23;

0.5 to 1 wt % Arnica;

1 to 10 wt % Aloe;

0.025 wt. % histimine; and the balance, a carrier.

The invention also applies to a method for making the cream comprising, the steps of mixing the preferred ingredients, heating the mixture to 60° C., adding the acetyl alcohol, the glycerol monosterate, the myristal myristate, the polysorbates and the titanium dioxide, then, one at a time, adding to the heated materials, benzyl alcohol, colloidal oatmeal, and lavender oil. While maintaining the temperature, the xanthum gum is dissolved into the propylene glycol, and uniphen P-23. The blended ingredients should then be removed from heat and the capsaicin should be dissolved into the benzyl alcohol the mixture is cooled to 40° C., the capsaicin is blended into the mixture forming the cream.

It should be understood that the foregoing relates only to a preferred embodiment of the present invention and that numerous modifications or alterations may be made therein without departing from the spirit and scope of the invention as set forth in the appended claims.

What is claimed is:

1. A cream comprising:

(a) a topical carrier wherein the topical carrier comprises a member selected from the group comprising lavender oil, myristal myristate, and other preservatives selected from the group consisting of *hypericum perforatum arnica montana* capric acid; and (b) 0.01 to 1.0 wt. % capsaicin;

(c) 2 to 10 wt. % an encapsulation agent selected from the group comprising colloidal oatmeal hydrogenated lecithin, dipotassium glycyrlhizinate and combinations thereof;

(d) esters of amino acid;

(e) a light scattering element having a particle size up to 100 nm.; and (f) a histidine.

2. A cream comprising:

0.01 to 0.25 wt % capsaicin;

1 to 10 wt % glyceryl monosterate;

1 to 10 wt % polysorbate;

5 to 15 wt % titanium dioxide;

5 to 14 wt % benzyl alcohol;

2 to 10 wt % colloidal oatmeal;

0.5 to 2 wt % lavender oil;

1 to 2 wt % propylene glycol;

0.001 to 0.005 wt % xanthum gum;

0.5 to 1 wt % arnica;

1 to 10 wt % aloe; and 0.25 wt. % histidine.

3. The cream of claim 1, wherein the carrier is selected from the group comprising: aqueous carriers, oil based carriers, fat based carriers, and fatty alcohol based carriers, and combinations thereof.

4. The cream of claim 1, wherein said capsaicin is selected from the group: nordihydrocapasaicin, capsaicin, dihydrocapsaicin, homocapsaicin, and combinations thereof.

5. The cream of claim 1, wherein said capsaicin is present in the range of from about 0.01 to about 1 percent by weight of said aqueous phase, lavender oil is present in the range of 1–3 wt % of said aqueous phase.

6. The cream of claim 1, wherein said capsaicin is in the range of 0.025 to 1 wt %.

7. The cream as in claim 6, wherein said capsaicin is in the range of 0.025% to 0.25% by weight.

8. The cream of claim 1, wherein said esters of amino acids are selected from the group: menthyl and lauryl esters of amino acids and combinations thereof.

9. The cream as in claim 8, wherein said esters of amino acid are between 0.10 wt. % and 1.0 wt %.

10. The cream as in claim 9, wherein said esters of amino acid are menthyl adequate to achieve 0.1 wt. % to 16 wt. % menthol in the formulation.

11. The cream of claim 10, wherein said ester is menthyl lauryl pidolate.

12. The cream of claim 1, wherein said light scattering element has a particle size of between about 30 microns and about 60 microns in diameter.

13. The cream of claim 1, wherein said light scattering element is selected from the group: titanium dioxide, zinc oxide, and benzophenones, methoxy cinnamate, para amino benzoic acid, octyl, dodecyl, neopentanoate, aluminum stearate with titanium dioxide, aluminum oxide with titanium dioxide, and combinations thereof.

14. The cream of claim 1, further comprises an additional anti-itch agent which is a member of the group: methyl sulphonyl methane, sodium bicarbonate, calamine, allantoin, kaolin, and combinations thereof.

15. The cream of claim 3, wherein the histidine is histamine dihydrochloride.

16. A patch for treating arthritis and neurological pains consisting of an elastomeric adhesive unit on which is disposed a formulation comprising:

(a) an effective amount to treat arthritis and neurological pains consisting of a topical carrier wherein the topical carrier further comprises a member of the group comprising lavender oil myristal myristate, and other preservatives selected from the group consisting of *hypericum perforatum arnica Montana,* capric acid and caprilic acid;

(b) 0.01 to 1 wt. % capsaicin;

(c) 2 to 10 wt. % an encapsulation agent selected from the group comprising colloidal oatmeal hydrogenated lecithin, dipotassium glycyrlhizinate and combinations thereof;

(d) esters of amino acid;

(e) a light scattering element having a particle size up to 100 nm.; and (f) a histidine.

* * * * *